United States Patent
Turri

(12) 
(10) Patent No.: US 6,346,113 B1
(45) Date of Patent: Feb. 12, 2002

(54) EAR-SPOON

(75) Inventor: Achille Turri, Morbio Inferiore (CH)

(73) Assignee: Arsline S.A., Vaccallo (CH)

( * ) Notice: Subject to any disclaimer, the term of this patent is extended or adjusted under 35 U.S.C. 154(b) by 0 days.

(21) Appl. No.: 09/380,741

(22) PCT Filed: Feb. 18, 1998

(86) PCT No.: PCT/CH98/00063

§ 371 Date: Sep. 13, 1999

§ 102(e) Date: Sep. 13, 1999

(87) PCT Pub. No.: WO98/42284

PCT Pub. Date: Oct. 1, 1998

(30) Foreign Application Priority Data

Mar. 24, 1997 (CH) .................................................. 707/97

(51) Int. Cl.[7] .................................................. A61F 9/00
(52) U.S. Cl. ..................................................... 606/162
(58) Field of Search ............................... 606/162, 161, 606/127, 160

(56) References Cited

U.S. PATENT DOCUMENTS

| | | | |
|---|---|---|---|
| 1,381,829 A | * 6/1921 | Hartman | ..................... 606/162 |
| 1,693,581 A | 11/1928 | Etling | |
| 1,980,826 A | 11/1934 | Reiss | |
| 2,096,162 A | * 10/1937 | Daley | ......................... 606/162 |
| 2,746,461 A | * 5/1956 | Bocchino | .................... 606/162 |
| 5,713,914 A | * 2/1998 | Lee | ............................. 606/162 |

FOREIGN PATENT DOCUMENTS

| | | |
|---|---|---|
| EP | 0 158 543 | 10/1985 |
| EP | 0556 432 | 8/1993 |
| FR | 1.582.734 | 10/1969 |

* cited by examiner

*Primary Examiner*—Kevin Truong
(74) *Attorney, Agent, or Firm*—Young & Thompson

(57) ABSTRACT

A multi-purpose and multi-use cleaning or treating device, in particular for personal hygiene includes at least a cleaning or treating head (20, 13). This head includes a substantially flat cleaning element (20) made of sponge plastic material capable of adopting any desired shape by the effect of forces applied thereon and to resume at least partially its original shape, preferably plane, when these forces are absent, and a support (13) whose shape the element (20) can match when it is folded down and arranged thereon for covering it at least partially. Retainer (30) co-operates with the element (20) and the handle (10) to ensure proper hold of the element on the support. The support (13) includes gripping means directly mounted, such as grooves, or intrinsic, by the very material of which the support is made, for example a resin or an elastomer. The supports can be of different shapes. This device can be made in the most varied dimensions, thereby making it useful for many different purposes (personal hygiene, medical or veterinary use, craftwork, in one dimension scale; industrial and domestic use in another dimension scale).

16 Claims, 3 Drawing Sheets

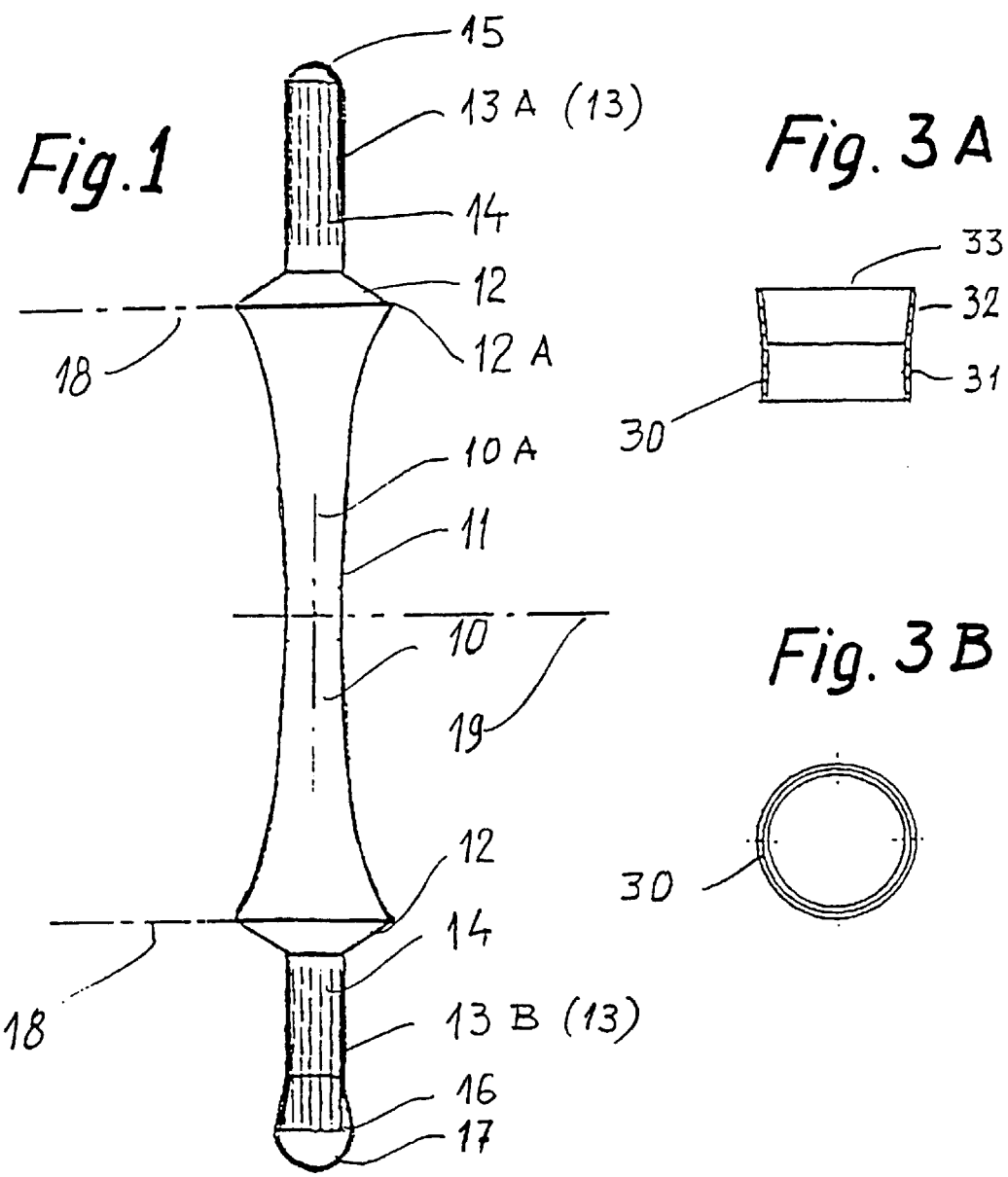

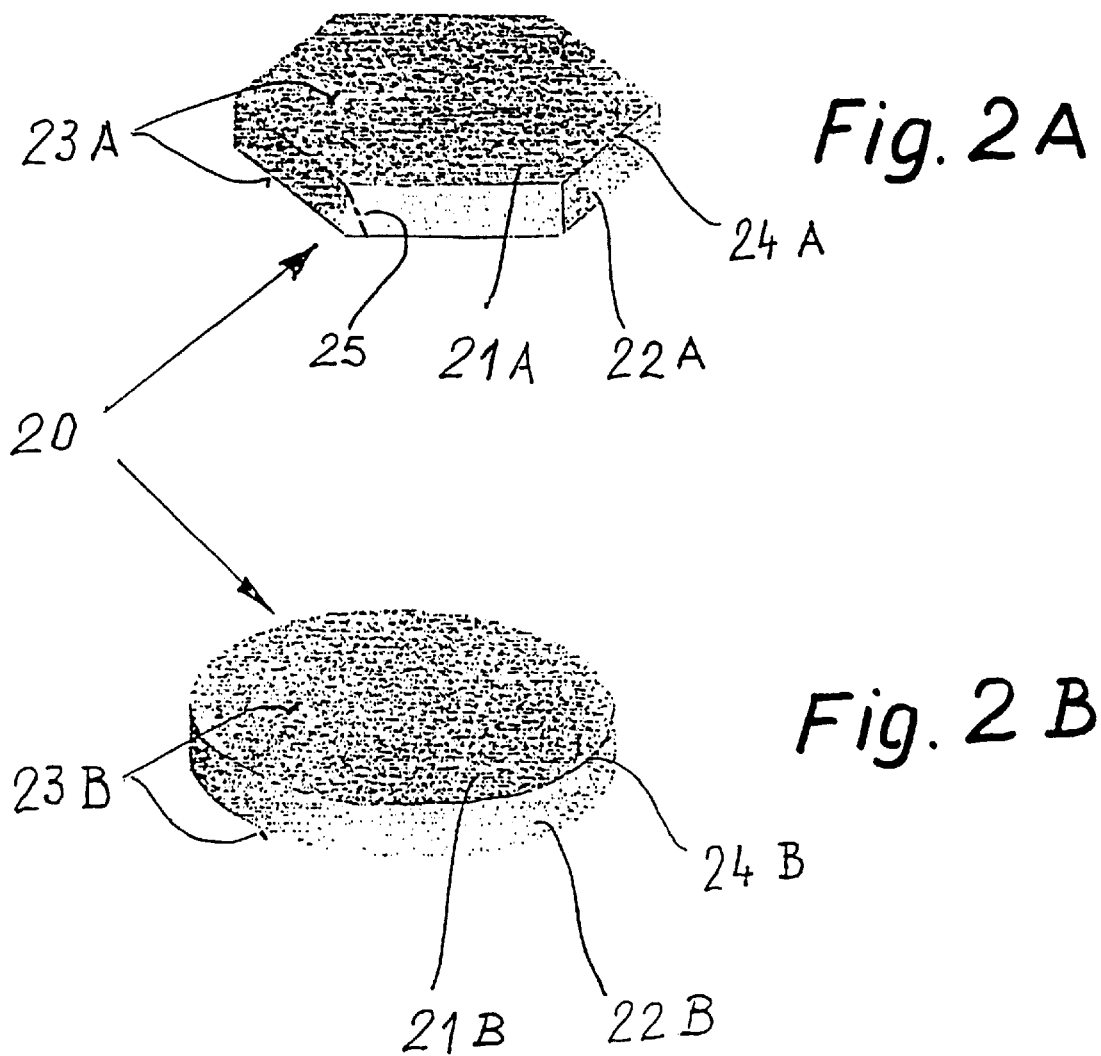

EAR-SPOON

BACKGROUND OF THE INVENTION

The present invention is related to a cleaning or treating utensil or tool having multiple utilities and applications, especially in personal hygiene Several products of this kind are known, especially, when personal hygiene is concerned, for example the cotton bud for cleaning the external auditory canal, this device being formed by a thin rod having on at least one of its ends a cleaning element, generally of cotton wool. The cotton buds are easy and inexpensive to manufacture; however, their cleaning power is rather low and limited. In fact, the cleaning head is small (its diameter does only slightly exceed that of the rod), and the user must make a rotational movement with his hand which has seized the cotton bud in order to make the head successively bear against all generatrices or sites within the duct or canal to be cleaned or treated. The degradation of the cleaning head caused by this rotational movement is rapidly accelerated when the user makes a second rotational movement with the rod which is superimposed on the first one, comprising a simultaneous rotation of the rod about its axis for improving the cleaning efficiency. Furthermore, the handling of the cotton bud is anything else than ideal and is even ineffective when a liquid has beforehand been introduced into the canal or when the head is impregnated with, for example, a pharmaceutical, cosmetic or detergent product before use (which will later on be called "active fluid"). Finally, in view of the diameter of the cotton buds, their use is not without risks to damage the eardrum. According to a more sophisticated execution, the heads of certain cotton buds have a bulge at their basis which limits the distance of the introduction into the canal and diminishes that risk (without, however, completely eliminating it) but does not lift the other disadvantages described above. For this reason, other devices have still been suggested, aiming at overcoming the disadvantages.

U.S. Pat. No. 1,693,581 discloses a cleaning instrument for the external auditory canal, comprising a handle, a support screwed to one end of the handle or being integral with it, an exchangeable cleaning piece (e.g., a piece of tissue or of leather), and a ring for holding this piece on the support. The said cleaning piece is put on the support and held thereon by a ring that cooperates with a conical seat of the support.

The document FR-1,582,734 describes a different applicator device where the cleaning head is of a poriferous matter.

The document EP-A-0,234,061 discloses an utensil for cleaning the auditory canal of the external ear, comprising a cleaning head of rubber plugged on the end portion of a small stick from which it may be removed. This head presents, seen from the front, the shape of a pear and has a star-shaped cross-section.

The document EP-A-0,184,237 describes a product of the same type, also consisting of two parts, namely the thin stick and a pluggable cleaning head, the latter optionally comprising a shoulder which has a stopper function in order to limit the penetration of said head into the auditory canal and avoiding to touch the eardrum. Seen from the front, this head has a cylindrical shape with rounded ends and its cross-section is in a variant also star-shaped.

The document DE-OS-4,117,526 goes in the same direction as the two European patent applications which have just been cited. The head is preferably oval and may be protected by a sliding ring when the product is not under use.

The document U.S. Pat. No. 1,980,826 describes an utensil for cleaning the external auditory canal, comprising a handle, a guard, and a cleaning head which is interchangeable according to some embodiments, said head comprising a threaded rod screwed into one end of the handle so that its length is adjustable but remaining sufficiently fixed against rotation during its use. The apparent portion of the cleaning head is made of rubber, of sponge rubber or of felt.

The recommended matter of the cleaning heads described in most of the documents of the prior art is a flexible and compact matter, rubber, tissue, leather or an equivalent one. However, the documents FR-1,582,734 and U.S. Pat. No. 1,980,826 teach the use of a spongy matter. In the DE-OS-4,117,526, the ribs or lamellas of the head may additionally be provided with nubs.

These references disclose of course improvements with respect to the cotton bud as far as the specific use in personal hygiene is concerned, but they do not satisfactorily brush aside the drawbacks of the cotton buds, discussed above in the first place. In fact, if it can be imagined that the rubber lamellas are bent during use—still under the condition that certain conditions regarding the dimension of said lamellas are respected (which may give rise to feasibility and reliability problems of the product which have not been discussed and still less resolved in the prior art)—, a continuous and uniform adaptation or conformation of the cleaning head to the surface or canal to be cleaned is not given. Furthermore, the cleaning heads have a predetermined shape that is fixed and compulsory forever. A specific shaping of the cleaning heads, whereas their action, as discussed above, does not really solve the problems, and the relatively complex means that are used, in particular in U.S. Pat. No. 1,980,826, enter to a sensible degree into the manufacturing costs of these instruments and raise them. Regarding the U.S. Pat. No. 1,693,581, the disadvantage of its object is obvious. In fact, it can easily be imagined that, when the described and defined object is put into use, the compact cleaning piece of flexible matter will necessarily curl up and slide around its support when the instrument is made to rotate, the only retention means being the maintaining ring. Finally, the applications remain essentially limited to the personal hygiene, more specifically to the cleaning of external auditory canals.

The present invention has the objective to overcome the technical as well as economical disadvantages of the known utensils.

A multi-purpose and multi-use cleaning or treating device, in particular for personal hygiene includes at least a cleaning or treating head. This head includes an element made of sponge plastic material capable of adopting any desired shape by the effect of forces applied thereon and to resume at least partially its original shape, preferably plane, when these forces are absent, and a support whose shape said element can match when it is folded down and arranged thereon for covering it at least partially. Retainer cooperates with the element and the handle to ensure proper hold of the element on the support. The support includes gripping means directly mounted, such as grooves, or intrinsic, by the very material of which the support is made, for example a resin or an elastomer. The supports can be of different shapes.

BRIEF DESCRIPTION OF THE DRAWINGS

An embodiment of the invention is now described in detail as a non-limiting example thereof, making reference to the drawing wherein:

FIG. 1 represents a possible shape of the instrument according to the invention, FIG. 2 shows the shape of the cleaning element before mounting, FIGS. 3A and 3B represent a holding piece for the cleaning element.

DESCRIPTION OF THE PREFERRED EMBODIMENTS

Figure 4:
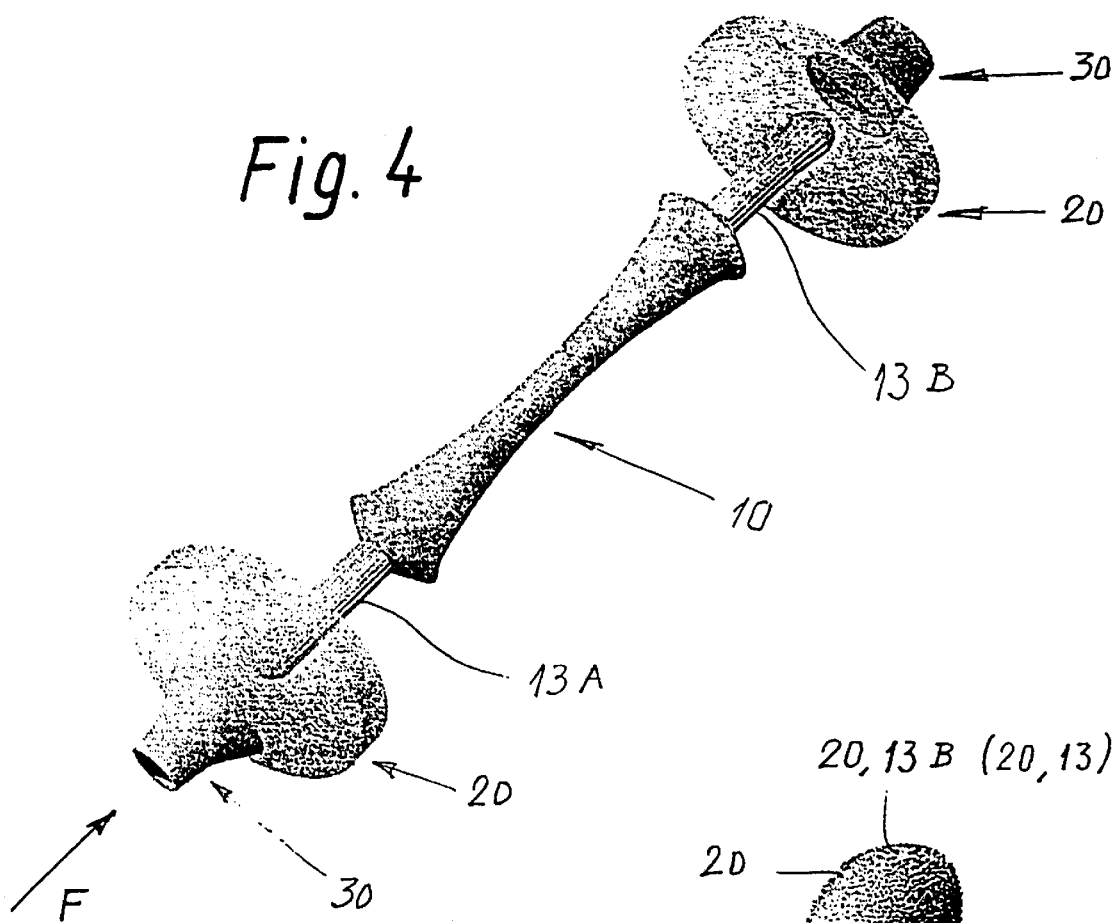
FIG. 4 shows the constituting parts of the instrument before assembling.

The utensil shown in FIG. 1 comprises a handle 10 having a symmetry axis 10A and a hyperboloid profile 11, and, on at least one of its two extremities, a shoulder 12 and a support 13, 13A, 13B. This shoulder has a truncated cone shape but may have any other profile, in particular hyperboloid, like the profile 11 cited above. The shapes of the supports are not necessarily identical. Thus, according to the non-limiting example shown in FIG. 1, it can be seen that the support 13A is cylindrical whereas the support 13B is cylindrical along a portion only of its length, the ending portion comprising a swelling 16 whose function will be explained later. The ends 15, 17 of the supports 13 are rounded. In a general manner, the support 13 will be addressed in the following as to design any support, whatever may be its shape. Finally, the shoulder and the support are preferably (but not necessarily) situated in the rectilinear prolongation of the axis 10A.

The support 13 is destined to receive (under the conditions to be described later on) a cleaning or treating element 20, two examples thereof being shown in FIGS. 2A and 2B. The element 20 is made preferably of a flexible and spongy matter, more generally of an alveolar matter such as a fine foam or sponge. The surface of the support 13 (i.e. the envelope of the support and not the rounded ends 15, 17) is provided with means for improving the hold of the cleaning element 20 on the support. These "holding" or gripping means will oppose a free rotation of said element or, at least, an unintentional one. According to an embodiment variant, this surface is provided at least in part with lengthwise directed grooves or streaks 14 having a triangular section and known per se (and which will be termed "built-up means"), which sensibly increase the friction coefficient between the contacting elements. According to another variant, the holding means, instead of being build-up, may be inherent or intrinsic to the selection of the material from which the support 13 is manufactured, namely, these holding means stem in this case from a property of said material, in the sense that the latter has not only an elevated frictional coefficient but also sufficient hardness and rigidity with respect to the charges to which the said support 13 may be exposed. As a matter of fact, if, on one hand, a gripping should be ascertained, it is also necessary, on the other hand, that the support 13 is capable of resisting to the compression forces or those which tend to bent it during the mounting of the cleaning element 20 on it and/or during the use of the instrument. The material of the support may thus be rubber, a resin, an elastomer or any other material capable of being formed under compressive conditions, it being essential that the selected material comprises the required above mentioned properties as to the friction coefficient and the sufficient rigidity). According to an embodiment of that second variant, only the envelope of the support 13 or that of the terminal portion thereof will be provided with the aforementioned selected material (having a high friction coefficient and a relatively high rigidity) whereas the remainder of the support 13 (thus at least its core) is made of any rigid material whatsoever (for example of a lightweight alloy). It is of course possible that the support 13, being provided with holding means inherent to the selected material, comprises also built-up gripping means of the aforesaid type.

FIGS. 2A and 2B represent the cleaning or treating element 20 which has the particularity of having, prior to its mounting on any one of the supports 13, the preferred shape of a flat piece (or a slightly concave one). As it has already been said, this element 20 is advantageously a fine natural or synthetic sponge (synthetic polyurethane foam of the ester or ether type) working at compression. Several shapes 21A, 21B are possible for this element 20 (outline, surface and thickness dimensions, see also the end of this paragraph regarding the surface dimensions). FIG. 2A shows a polygonal element 20 (here: hexagonal element 22A). This outline is referenced 22A, an edge 24A, and the two surfaces, 23A. FIG. 2B shows a circular element 20 having a circumference 22B, an edge 24B, and two surfaces 23B. In the following, the letters will be left out, and in a general manner, one describes a cleaning element 20, a shape 21, a circumference 22, a surface 23 and an edge 24. In the folded or bent down condition onto the support 13, see below, the circumference 22 of the cleaning element 20 will be applied against the support 13 or the supporting surface 12, or it will be situated at least in the vicinity of that surface, the element 20 thus entirely or at least partially covering said support. This will say that the shapes of the element 20 (see the aforesaid exception) are preferably defined such that, in the folded down state, said circumference or better an edge 24 (see also FIG. 4) or at least portions of it, confined and wrinkled around the support 13 or the shoulder 12, will be situated approximately at the height of a plane 18 (symbolized by a dashed line in FIG. 1). The circumference 22 may be cut at an angle, see reference 25 in FIG. 2A. In other words, the straight sections (perpendicular to the surfaces 23) of the element 20, not shown, and independently on the shape 21, may be trapezoidal instead of rectangular. According to a variant, the cleaning element 20 has in its central region a higher thickness than over the remaining surface. In this manner, the cleaning element exerts a higher resistance against the force loaded on it in this region during mounting (see below).

Figure 5:
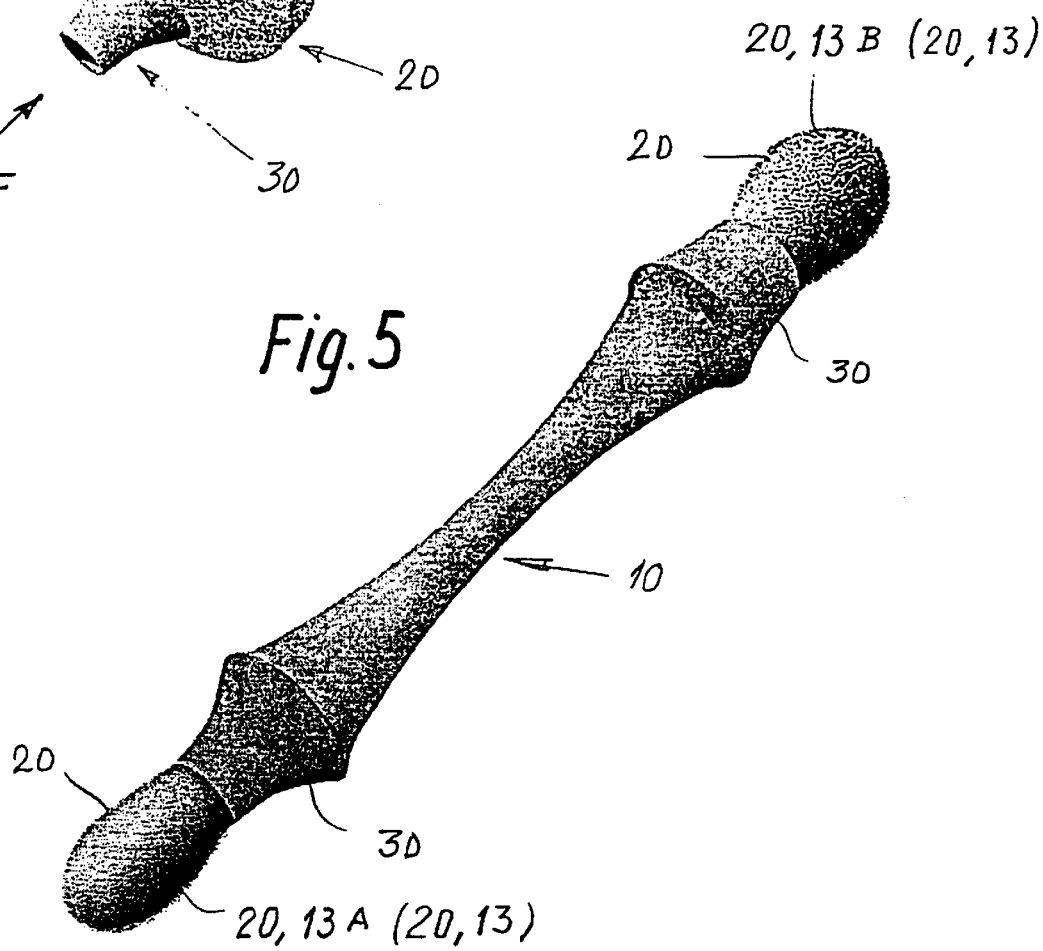
FIG. 5 represents the instrument according to the invention in assembled state (it should be noticed that the pieces and elements that are shown are not always at the same scale).

FIGS. 3A and 3B show a sectional view and a view from above of an auxiliary piece 30 having a holding function, namely, according to the example, a tubular ferrule destined to cooperate, during the fastening of said element on any one of the supports 13, with the cleaning element 20, at one hand, and the handle 10 or, more precisely, the edge 12A of the shoulder 12 on which the piece 30 is supported (see also FIGS. 4 and 5). This piece 30 which will be named "holding piece" or "retaining piece" or "ferrule", may be present in several shapes. According to the described variant, it is bell-shaped. The ferrule 30 is namely composed of an essentially cylindrical portion 31 and, in its prolongation, a truncated cone portion 32 whose aperture angle is preferably in the order of 60°. Like the support 13, the whole or a part of the inner surface of the ferrule 30 (preferably only the cylindrical portion 31) advantageously comprises means for improving the holding force applied by the cleaning element 20, i.e., for example, lengthwise directed grooves (not shown). According to a preferred embodiment, the ferrule 30 is rigid. But it is also possible to provide a flexible holding piece, for example of synthetic material such as of elastic material which exerts a pressure against the element 20 for retaining it against the support 13. In this case, it will not be provided with gripping means.

The mounting of the cleaning element 20 on a support 13 is effected in an extremely simple and rapid manner to be understood in looking at FIG. 4, thanks to the above-indicated properties of the selected material, on one hand, and to the choice of the preferred holding means of the element 20, on the other hand (it is considered here that the used ferrule is rigid). In fact, it will be sufficient to first lay the element 20 down on the ferrule 30 so that the axes (not shown) of the two parts are falling more or less together (as it can be seen in FIG. 4), the element 20, and according to a variant, the thickest portion of this element being pushed against the widest portion of the bell, i.e. against the edge 33 (FIGS. 3A and 4), and then to apply the center of the assembly 20, 30 against the rounding 15 or 17 of the support 13. Finally, in a third step, the assembly 20, 30 is pushed onto the support 13 towards the shoulder 12 in applying a force in the direction of the arrow F. During this operation, the element 20 is still further bent and takes the shape of the support 13 and covers it whereas the ferrule is pushed against the shoulder 12 of the handle 10. Here rises the advantage of reinforcing the cleaning element in its central region, e.g. by providing a greater thickness of the said element in said zone. When the described operations are finished, the ferrule 30 whose edge 33 is in contact with the edge 12A of the shoulder 12, covers a portion of the element 20 whereas the emerging portion of the cylindrical section 31 forms, together with the support 13, a cleaning or treating head 20, 13. The edge 33 is manufactured in such a manner that it does not damage the element 20 during the operations of mounting and removal; it is preferably rounded or provided with a rim (these particulars are not shown in FIGS. 3A, 3B and 4). In order to remove said element 20 from its support 13, the inverse operations are carried out, i.e. a force F' (not shown in FIG. 4) is exerted in the inverse direction of the force F and of equivalent intensity (FIG. 4), and the element 20 recovers automatically during its liberation its initial shape (a plain form in the described Example).

It can be seen that the profile of the support 13A is different from that of support 13B. Since the element 20 is of a flexible material, preferably a sponge, cleaning heads are obtained having different shapes (i.e., when seen in the direction of axis 10A of the rod 10, with different diameters), and this with the same standard element 20. In this way, the user may easily establish a set of pieces 20, 30 on one of the supports and afterwards mount the same set on the other support that has a different shape, according to the object to be attained, one shape being better fitted for a specific use than another, or still following an intensive cleaning of the element or elements 20. These advantages are as more important as they continue an obvious economical advantage, regarding the costs of manufacture and of the use of the instrument as well. It should be added in this context that it is of course more advantageous to mount a cleaning element 20 on both supports, and the utensil looks as shown in FIG. 5.

The assembly 20, 30 remains fixed owing to the action of a group of means or preferably owing to combined actions of a first group of means and a second one. The first group of means is formed by gripping means which may advantageously be constituted, according to a variant, by the means 14 provided on the support 13 or, in another variant, the means resulting from the very material of which the support 13 is entirely or partially made. Furthermore, that first group of means may be completed by gripping means of the same kind provided at the inside of the ferrule or provided by the very material of the ferrule. In a general manner, when built-up means are concerned, the friction coefficient may still be increased by a relatively rough shaping of the said gripping means, namely in leaving a roughness on the edge lines of the grooves. The second group of means results from the reaction forces of the spongy element 20 on the ferrule 30, taking into account the opening diameter of the tube 31, this diameter being adapted to the dimensions of the support 13 (i.e. to the diameter of said support if it is cylindrical) and to the appropriate thickness of the cleaning element 20. The spongy material within the region of the conical portion 32 of the ferrule 30 may of course somewhat expand, taking into account the profile of the shoulder 12 (having according to the example shown in FIGS. 1 and 4 a conicity that is essentially greater than that of the portion 32 of the ferrule 30), but this does not prejudice the reliability of the assembly since a thrust remains applied to the ferrule by the portion of the element 20 imprisoned therein, the element 20 having the tendency to recover its flat or nearly flat conformation. Moreover, he bell shape of the ferrule has another double advantage, namely ergonomy since it allows an easy manipulation during "capping" of the element 20 onto the support 13 and the "decapping", and aesthetic since it is in harmony with that of the handle 10. The holding piece 30, ascertaining the folded-over position of the cleaning element 20, is at the same time retained itself against any displacement owing to said thrust exerted on it by the said element 20.

In a general manner, the dimensions of the different pieces and piece portions 10, 12, 13, 20, 30 that compose the utensil should be adapted mutually and to the use or field of use; this is up to the one skilled in the art. As to the constitution of the different parts 10, 12, 13 and 30, any appropriate material or material combination whatsoever (light metal, synthetic materials) may be used, with the reserve of course as to the material of the support 13, according to the embodiment variant.

According to an embodiment not shown, the ferrule 30 and the handle 10 may comprise complementary retaining or fixing means, known to the one skilled in the art (clamps, forks, clips, etc.) coacting with each other in order to ascertain a connection with the handle 10 and, at the same time, the holding of the elements 20 and 30. Such means are preferably disposed within the border region 33 of the ferrule and at the shoulder 12 or the region 12A of the handle 10. These means are recommended for instruments of greater size destined for other applications (see below).

According to still another embodiment (not shown either), the number of supports 13 may be increased in selecting a multibranch handle. This is to say that, as an example, the handle may have the shape of a cross-piece having two branches, one according to the axis 10 and the other along the axis 19 (FIG. 1), each branch bearing at least one support and each support having optionally a specific shape.

It would also be possible to provide a monolithic execution of the utensil, for example by gluing the cleaning element 20 to the support 13 with or without ferrule: in this case, the function of the auxiliary holding means is taken over by the glue. When the wear of the element 20 requires an intervention, the user can remove the worn-out element (and this worn-out element will be partially destroyed) and replace it by a new element that is glued onto the support 13.

When the element 20 is constituted of a spongy matter, it works at compression in a manner that, when it is applied to the surface to be cleaned or treated, or during its introduction in, e.g., the external auditory canal of the ear to be treated or cleaned, it will be compressed, and a portion at least of its envelope (namely the external and active surface 23 of the head 20, 13) exerts simultaneously on that surface or canal a reaction force each time perpendicular to the plane tangent to the envelope. In other words, the element 20 is continuously and uniformly pressed against the surface or the duct during the cleaning or treating operation. The cleaning power of the head 20, 13 is optimal since the sponge is characterized by the combination of a certain hardness due to the material itself, thus having an ideal abrasion degree for cleaning purposes; and, on the other hand, a flexibility brought about by the presence of cavities, that flexibility being modulated by or function of the density and the dimensions of these cavities, the particles to be eliminated (for example the cerumen when the utensil is used for cleaning the external auditory canal) being captioned by the latter and easily removable by simple rinsing of the head 20, 13.

The other important advantage of the utensil according to the invention is based on the fact that it is ideally suited for a "humid" as well as for a "dry" work, because the spongy material allows to absorb an active fluid for a determined purpose and then to uniformly liberate this fluid with the duct, the cleaning head exerting at the same time a distributing function by successive and continuous absorption and liberation of the active fluid additionally to the cleaning function, or exerting a rinsing or drying function.

Still another advantage is established by the multiplicity of application fields where the utensil of the invention may be used, owing to the fact that it may be manufactured at very different scales, the principle of the means, their shapes and their functions remaining the same. Thus, the utensil may be manufactured with usual and known dimensions (total length of the utensil in the order of ten centimeters) for not only medical, veterinary, personal hygienic, cosmetic and making-up purposes, but also for all other utilities such as coloring, painting or do-it-yourself. Other, totally different applications may also be considered, especially in the field of household or industrial cleaning. In this case, it will be sufficient to define other dimensions for the constituting elements of the utensil, each time adapted to the particular field of use.

The implementation of the invention in most diverse application fields is as more interesting and recommended as the cleaning elements or heads can be easily and effectively rinsed and cleaned and even sterilized after every use (which would perhaps not work with the embodiment where the cleaning element is glued on the support).

The utensil according to the invention combines effectiveness with a low priced manufacture, and it may easily be imagined that its presentation may be widely varied (according to the preferred embodiment, the different elements such as handle, cleaning elements and ferrules may be sold separately), and that its possible applications are virtually unlimited.

What is claimed is:

1. Cleaning or treatment utensil, comprising:
    at least one handle (10),
    at least one support (13) destined to be capped by a cleaning element (20) to form with the support (13) a cleaning head (20, 13), and
    at least one holding piece (30), wherein the cleaning element (20) is an interchangeable piece having a circular or polygonal circumference (22), in that said interchangeable piece is substantially flat and constituted by a flexible material allowing its adaptation to any desired shape under the effect of forces applied to said interchangeable piece and the at least partial recovery of its initial shape in the absence of these forces, in such a manner that said element (20) molds to the shape of the support (13) when it is disposed on said support (13) for capping at least partially the latter and being retained thereon by the holding piece (30), said flexible material working at compression,
    wherein the support (13) comprises gripping means (14) opposing a free rotation of the element (20) situated on the support, and
    wherein the holding piece (30) ascertaining the holding of the element (20) on the support (13) is retained itself by the action exerted on it by said element (20).

2. Utensil according to claim 1, wherein the gripping means (14) are intrinsic means resultant from the choice of an appropriate material for the at least partial constitution of the support (13).

3. Utensil according to claim 2, wherein the material comprising said intrinsic means combines a defined rigidity with a high friction coefficient, this material being a resin or an elastomer.

4. Utensil according to claim 1, wherein the support (13) is specifically shaped.

5. Utensil according to claim 1, wherein the material constituting the element (20) is a fine sponge.

6. Utensil according to claim 1, wherein the holding piece (30) partially recovers the element (20) and comprises means opposing a free mutual rotation of said holding piece (30) and said element (20).

7. Utensil according to claim 1, wherein the holding piece (30) is approximately bell shaped, comprising an essentially cylindrical portion (31) and an essentially conical portion (32) whose widened border (33) comes into contact with the handle (10).

8. Utensil according to claim 1, wherein the dimensions of the element (20) are such that, when disposed on the support (13), at least parts of the circumference (22) of said element are situated approximately in a plane (18) of the handle (10).

9. Utensil according to claim 8, wherein the plane (18) is situated within the widest zone (12A) of a shoulder (12).

10. Utensil according to claim 1, wherein the handle has a hyperboloid profile, and that the support (13) is connected to said handle by a shoulder (12) on which the holding element (30) is supported.

11. Utensil according to claim 1, wherein the support (13) is situated in the prolongation of the axis (10A) of the handle (10).

12. Utensil according to claim 1, wherein the holding piece (30) and the handle (10) comprise complementary retaining means cooperating with each other.

13. Utensil according to claim 12, wherein the complementary retaining means of the element (20) on the support (13) is glue.

14. Utensil according to claim 1, wherein the handle has two ends, each carrying the support (13).

15. Utensil according to claim 1, wherein the means (14) of the support (13) which oppose the rotation of the element (20) of the head (20, 13) are grooves or streaks having a triangular section and exerting a gripping action to said element (20).

16. A cleaning utensil comprising:
    a handle;
    a generally cylindrical support with a rounded tip, at an end of said handle;

a cleaning element that is generally flat and flexibly adaptable to a shape of said support when placed and held thereon and that has a recovery force that returns said cleaning element approximately to an initial shape when said cleaning element is removed from being held on said support; and a tubular holding piece that removably slides over said cleaning element and said support and holds said cleaning element on said support and forces said cleaning element to conform to a shape of said support, said holding piece exposing a portion of said cleaning element conforming to a shape of said rounded tip of said support, said holding piece being held on said cleaning element by said recovery force.

* * * * *